United States Patent [19]

Hoffmann et al.

[11] Patent Number: 4,662,370

[45] Date of Patent: May 5, 1987

[54] APPARATUS FOR PERFORMING LAMELLAR REFRACTIVE CORNEAL SURGERY

[75] Inventors: Friedrich Hoffmann; Kai Jessen, both of Berlin, Fed. Rep. of Germany

[73] Assignee: Carl-Zeiss-Stiftung, Heidenheim, Fed. Rep. of Germany

[21] Appl. No.: 671,301

[22] Filed: Nov. 14, 1984

[30] Foreign Application Priority Data

Sep. 13, 1984 [DE] Fed. Rep. of Germany ....... 3433581

[51] Int. Cl.⁴ .............................................. A61F 9/00
[52] U.S. Cl. ..................................... 128/305; 128/310
[58] Field of Search ..................... 128/305, 310, 305.1, 128/753, 754

[56] References Cited

U.S. PATENT DOCUMENTS 4,205,682  6/1980  Crock et al. ......................... 128/305
4,429,696  2/1984  Hanna ................................ 128/305

Primary Examiner—Gene Mancene
Assistant Examiner—David I. Tarnoff
Attorney, Agent, or Firm—Walter Ottesen

[57] ABSTRACT

An apparatus for performing lamellar refractive corneal surgery includes a base ring adapted for seating on the sclera of the eye to be operated upon. A planar plate is fixedly attached to this base ring so that the mutually adjacent surfaces of the plate and the base ring conjointly define an air gap. As oscillating knife is guided in this air gap during the cutting process and is moved in a guide connected to the base ring. The surface of the planar plate facing the eye contains an applanate surface which is preferably defined by the end face of an insert inserted into the planar plate. A ring-shaped recess open toward the eye concentrically surrounds the insert and communicates with a conduit to which a partial vacuum can be applied.

8 Claims, 4 Drawing Figures

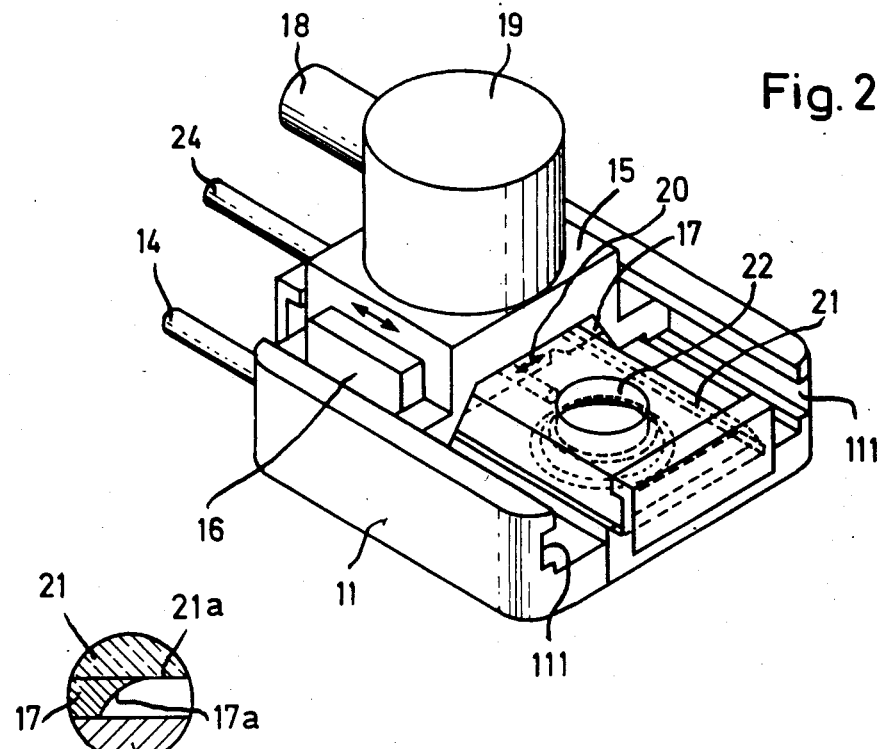
Fig. 2
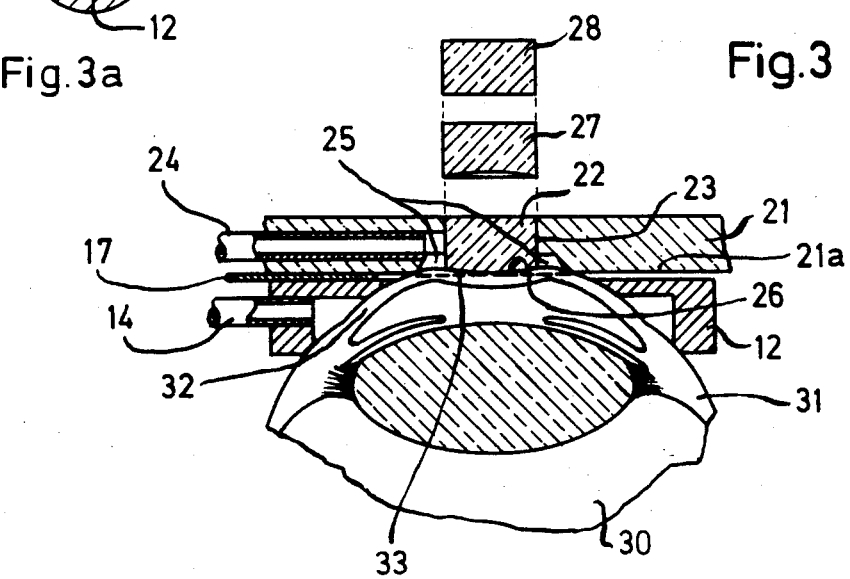
Fig. 3a
Fig. 3

APPARATUS FOR PERFORMING LAMELLAR REFRACTIVE CORNEAL SURGERY

FIELD OF THE INVENTION

The invention relates to an apparatus for performing lamellar refractive corneal surgery and includes a base which is held in a fixed position on the eye to be operated on with the aid of a partial vacuum. An oscillating knife is mounted on a support which, in turn, is guidably mounted on the base for movement over the eye.

BACKGROUND OF THE INVENTION

In the case of an eye with emmetropia (normal vision), an object at infinity will be imaged on the retina located at the rear of the eyeball. In an eye having poor vision, such an object is imaged on the retina unclearly in the form of dispersion circles.

In the case of myopia (nearsightedness), a distant object is sharply imaged in front of the retina. This is caused by the fact that a myopic eye either has a length which is too large in relationship to the refractive power of the normal eye or too high a refractive power in relationship to the length of the normal eye. Too high a refractive power of the eye is caused by the cornea of the eye having too great a curvature.

In the case of hyperopia (farsightedness), a remote object is sharply imaged behind the retina. In this situation, either the length of the eye is too short or the refractive power of the eye is too low.

Especially in the case of persons born with myopia, attempts have been made to reduce the refractive power of the eye with the aid of refractive corneal surgery which reduces the curvature of the cornea.

One known solution is radial keratotomy wherein up to 16 radial cuts are made in the cornea of varying length and depth. This leads to a flattening of the central corneal region which effects a correction of 2 to 6 diopters. A correction achieved by the operation is as a rule substantially reduced in the first few months thereafter.

From German published patent application DE-OS No. 32-15 832, it is also known to make a circular incision in the cornea of the eye concentric to the optical zone which too leads to a central flattening of the cornea. A circular insert is placed in this incision which holds the cornea in its flattened position.

A microkeratom was developed by J. I. Barraquer and is shown in FIG. 1 of the drawing and, with the aid of which, it is possible to cut off a corneal lamella parallel to the surface of the cornea. In this connection, reference may be made to an article by J. I. Barraquer in "Archivos De La Sociedad Americana Oftalmologia" Volume 6, (1967) pages 69 to 101. This microkeratom is made up of a base ring which is seated upon the eye to be operated and fixed there in position with the aid of a partial vacuum. A support is guidably mounted for movement on the base ring and moves an oscillating knife across the eye. The device includes an applanate surface against which the corneal surface lies during the movement of the knife. When the oscillating knife is moved across the eye lying against the applanate surface, a lamella is cut off which is parallel to the surface of the cornea lying against the applanate surface.

The corneal lamella separated in this manner is frozen pursuant to the method which is known as keratomileusis and, in this condition, is processed on a rotating worktable for frozen materials. For example, it can be thinned at the central region and then sewn onto the patient's eye. This process is imprecise because changes in the volume of the corneal lamella can occur in the freezing process. The process has also the medical disadvantage that the previously frozen corneal lamella can cause long-lasting irritations of the corneal surface.

With keratophakia, lens tissue from donor corneal material is placed between the cornea and the corneal lamella which was surgically removed from the patient's eye. The lamella is then secured. Here too, the donor cornea is processed in the frozen condition.

The same is true also for epikeratophakia wherein a lamella-shaped lens made from donor cornea is placed upon the cornea of the patient's eye and sewn thereon after the epithelium is removed.

With all such surgical methods, an interlamellar corneal scar is formed which is dependent upon the quality of the corneal cut.

SUMMARY OF THE INVENTION

It is an object of the invention to provide an apparatus for performing lamellar refractive corneal surgery which makes it possible to decrease or increase the radius of curvature of the cornea of a patient's eye in a predetermined way.

With the apparatus of the invention, the radius of curvature of the cornea after the cut is determined by the form of the applanate surface against which the surface of the cornea of the patient's eye lies when the cut is made.

The oscillating knife is guided exactly parallel to the planar surface of the planar plate during the cut. If the applanate surface has a convex form, the corneal lamellar cut is thinner in the center than at its periphery, that is, the curvature of the corneal lens is thereby increased. By utilizing a concave applanate surface, the curvature of the corneal lens thereby formed is reduced as is possible during the operative treatment for myopia. By utilizing a planar applanate surface, a corneal lamella can be removed by a cut which is parallel to the top surface of the cornea.

The apparatus of the invention has the advantage that it makes it possible to cut the cornea of the patient's eye so that a lens of a predetermined form and curvature results which is made up of the patient's own tissue which is unchanged. The freezing process which is otherwise required is thereby eliminated.

The apparatus according to the invention is applicable to many situations because of the exchangeability of the applanate surface. Very precise results are obtained because only the oscillating knife is moved across the eye during the cutting operation and the eye is fixed in position against the applanate surface.

BRIEF DESCRIPTION OF THE DRAWING

The invention will now be described with reference to the drawing wherein:

FIG. 2 is a perspective schematic of an embodiment of the apparatus according to the invention;

FIG. 3 is a section view of a portion of the apparatus according to the invention taken through the longitudinal axis thereof; and, FIG. 3a is an exploded view of a portion of FIG. 3 and shows the cutting edge of the knife of the apparatus according to one embodiment of the invention.

DESCRIPTION OF THE PREFERRED EMBODIMENTS OF THE INVENTION

Figure 1:
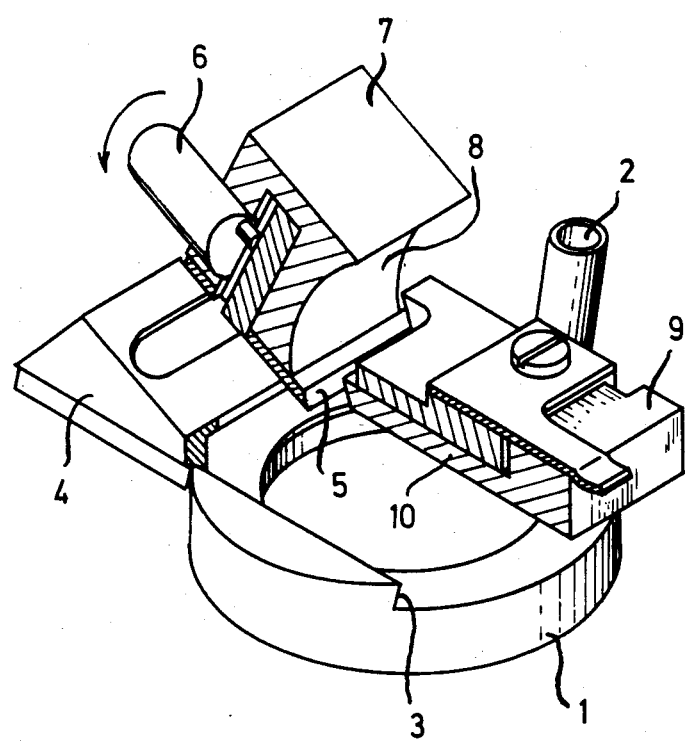
FIG. 1 is a perspective view of a microkeratom according to Barraquer.

The known microkeratom of FIG. 1 includes a suction ring 1 which is placed upon the patient's eye and is fixed in position thereupon when a partial vacuum is applied via conduit line 2. The suction ring 1 is provided with a guide 3 for a support 4. A knife 5 is mounted on the support 4 and is arranged at an angle of 25° with respect to the cutting plane. The knife 5 is caused to go through an oscillatory movement by eccentric member 6. The knife 5 moves in a slit formed between support 4 and a part 7. The part 7 defines a diverting surface 8 for receiving the corneal lamellar cut from the patient's cornea. A spacer plate 9 is fixedly attached to the support 4 and has a lower surface 10 which functions as an applanate surface for the patient's eye.

To perform the operation, the suction ring 1 is fixed in position on the patient's eye and the oscillating knife 5 together with the support 4 and the spacer plate 9 are moved across the eye of the patient. During the cutting procedure, the applanate surface 10 glides over the top surface of the cornea so that a corneal lamella is cut off which is parallel to this surface. This corneal lamella is processed as previously described.

The embodiment of the apparatus according to the invention shown in FIGS. 2 and 3 includes a base plate 11 having a suction ring 12 which forms an integral part thereof. The suction ring 12 communicates with a conduit 14 through which a partial vacuum can be applied. The base plate 11 includes slide bearings 111 of the support 15. A knife holder 16 is secured to the support 15 and a knife 17 preferably made of sapphire is clamped in the holder 16. The knife 17 is caused to undergo an oscillatory movement by drive means 18 and angular gear means 19. The direction of oscillatory movement is indicated by arrow 20.

A planar plate 21 is fixedly mounted to the base plate 11 and includes a bore 23 for receiving an insert 22 in a vacuum-tight manner. As shown in FIG. 3, the end of the bore 23 facing toward the eye is surrounded by an annulus 25 open toward the eye and communicating with a conduit 24 through which a partial vacuum is applied to the annular space 25.

The insert 22 is tapered to ensure a vacuum-tight seat in the bore 23. The end face 26 of the insert 22 seated in the bore 23 has a convex configuration. Other inserts 27 and 28 having end faces facing the eye which are concave and planar, respectively, can also be inserted as required. The form of this end face determines the form and function of the corneal lens produced by the operation.

When performing the operation, the apparatus shown in FIG. 2 is placed upon the eye 30 of the patient as shown in FIG. 3. The suction ring 12 is thereby caused to lie upon the sclera 31 of the eye 30. The ring 12 is fixed in position by applying a partial vacuum at the conduit 14. A partial vacuum is applied to conduit 24 after the insert 22, 27 or 28 suitable for the particular application is inserted in the bore 23 of the planar plate 21. As a consequence thereof, the central part of the cornea 32 lies against the end face 26 of the insert 22. The cornea 32 is shaped in correspondence to the form of the applanate surface 26. Now the support 15 with the oscillating knife 17 is moved in the air gap between the suction ring 12 and the planar plate 21 and thereby cuts off a corneal lamella along the cutting line 33. After this cutting step, the apparatus is removed from the eye. The remaining cornea 32 then again takes on its original form whereby the cut surface of the cornea in the example of FIG. 3 has a curvature which is increased over that which it had before the operation.

Now a plane parallel lamella is cut from the donor eye utilizing the insert 28 and sewn to the patient's eye.

The oscillating knife 17 is advantageously made of sapphire. On the one hand, a rubbing between the knife and the cornea is thereby decreased and, on the other hand, a higher durability of the knife 17 is achieved. The knife 17 as shown in FIG. 3 has a concave bevel 17a (FIG. 3a) on one side and has a cutting edge that faces toward the surface 21a of the planar plate 21 facing the eye. In this way, the amount of power needed during the cutting operation is reduced to a minimum and the cut surfaces are of a very good quality.

The planar plate 21 and the inserts 22, 27 and 28 are all made of transparent material in order to make an exact positioning of the suction ring 12 on the sclera 31 of the eye 30 possible.

It is understood that the foregoing description is that of the preferred embodiments of the invention and that various changes and modifications may be made thereto without departing from the spirit and scope of the invention as defined in the appended claims.

What is claimed is:

1. Apparatus for performing lamellar refractive corneal surgery on a cornea having a given radius of curvature, the apparatus comprising:

a base adapted for placement on the sclera of the eye on which the surgery is to be performed;

said base having an annular recess formed therein to define a chamber with said sclera when said base is placed thereon;

vacuum means for developing a partial vacuum in said chamber thereby fixing said base on the eye;

a support body guidably mounted on said base for movement over the eye;

knife means mounted on said support body for movement therewith to perform a surgical cut on the cornea of the eye;

a flat plate fixedly mounted on said base and having a lower surface facing the eye;

said base having an upper surface facing said lower surface of said plate;

said surfaces conjointly defining an air gap therebetween for guiding said knife means therein during the cutting step;

applanate surface means in said lower surface of said flat plate for receiving the surface of the cornea thereagainst;

annular recess means disposed in surrounding relationship to said applanate surface means to define a chamber with the cornea; and, ancillary vacuum means for developing a partial vacuum in said last-mentioned chamber so as to cause said cornea to be pressed against said applanate surface means thereby placing the same in position preparatory to the surgical cut; and, said applanate surface means having a preselected contour for imparting a predetermined shape to the cornea when the latter is pressed thereagainst thereby causing said radius of curvature of the cornea to be changed by a predetermined amount upon completion of said surgical cut.

2. The apparatus of claim 1, said annular recess being concentric to said applanate surface means; and, said knife means comprising: a knife blade guidably mounted in said air gap between said upper surface of said base and said lower surface of said flat plate; and, means for imparting an oscillatory movement to said knife blade in a direction transverse to the direction of the movement thereof along said air gap.

3. Apparatus for performing lamellar refractive corneal surgery comprising:
- a base adapted for placement on the sclera of the eye on which the surgery is to be performed;
- said base having an annular recess formed therein to define a chamber with said sclera when said base is placed thereon;
- vacuum means for developing a partial vacuum in said chamber thereby fixing said base on the eye;
- a support body guidably mounted on said base for movement over the eye;
- knife means mounted on said support body for movement therewith to perform a surgical cut on the cornea of the eye;
- a flat plate fixedly mounted on said base and having a lower surface facing the eye;
- said base having an upper surface facing said lower surface of said plate;
- said surfaces conjointly defining an air gap therebetween for guiding said knife means therein during the cutting step;
- applanate surface means in said lower surface of said flat plate for receiving the surface of the cornea thereagainst so as to impart a predetermined shape to the latter;
- annular recess means concentric to said applanate surface means and being disposed in surrounding relationship to said applanate surface means to define a chamber with the cornea;
- said knife means including: a knife blade guidably mounted in said air gap between said upper surface of said base and said lower surface of said flat plate; and, means for imparting an oscillatory movement to said knife blade in a direction transverse to the direction of the movement thereof along said air gap;
- ancillary vacuum means for developing a partial vacuum in said last-mentioned chamber so as to cause said cornea to be pressed against said applanate surface means thereby placing the same in position preparatory to the surgical cut; and,
- said applanate surface means including: bore means formed in said flat plate and extending therethrough so as to communicate with the cornea; and, a plurality of inserts selectively and exchangeably insertable into said bore means so as to engage the latter in a vacuum-tight manner, said inserts having respective end faces facing toward the cornea when inserted in said bore means, said end faces defining respectively different applanate surfaces for receiving the cornea thereagainst in the presence of a partial vacuum in said last-mentioned chamber.

4. The apparatus of claim 3, said plurality of inserts being three in number and said applanate surfaces corresponding thereto being of planar, convex and concave configuration.

5. The apparatus of claim 3, flat plate and said inserts all being made of a transparent material.

6. The apparatus of claim 5, said knife blade being made of sapphire.

7. The apparatus of claim 6, said knife blade having a concave bevel formed therein to define the cutting edge thereof, said knife being mounted in said air gap so as to cause said edge to be directly next to said lower surface of said flat plate.

8. Apparatus for performing lamellar refractive corneal surgery comprising:
- a base adapted for placement on the sclera of the eye on which the surgery is to be performed;
- first vacuum means for fixing said base in position on the sclera during the surgery;
- a support body guidably mounted on said base for movement over the eye;
- knife means mounted on said support body for movement therewith to perform a surgical cut on the cornea of the eye;
- a flat plate fixedly mounted on said base and having a lower surface facing the eye; said base having an upper surface facing said lower surface of said plate;
- said surfaces conjointly defining an air gap therebetween for guiding said knife means therein during the cutting step;
- said flat plate including applanate surface means in said lower surface thereof for receiving the surface of the cornea thereagainst so as to impart a predetermined shape to the latter; and,
- second vacuum means for pressing the cornea against said applanate surface means thereby placing the same in position preparatory to said surgical cut.

* * * * *